United States Patent

Kawashima et al.

Patent Number: 4,952,689
Date of Patent: Aug. 28, 1990

[54] 3-(SUBSTITUTED PROPYLIDENE)-2-AZETIDINONE DERIVATIVES FOR BLOOD PLATELET AGGRGATION

[75] Inventors: Yutaka Kawashima, Tatebayashi; Masakazu Sato, Konosu; Masahiro Kawase, Ageo; Yoshiaki Watanabe, Kodaira; Katsuo Hatayama, Omiya, all of Japan

[73] Assignee: Taisho Pharmaceutical Co., Ltd., Japan

[21] Appl. No.: 419,206

[22] Filed: Oct. 10, 1989

[30] Foreign Application Priority Data

Oct. 20, 1988 [JP] Japan .................................. 63-265183

[51] Int. Cl.$^5$ ................. C07D 205/08; A61K 31/535; A61K 31/445; A61K 31/395
[52] U.S. Cl. ...................................... 540/200; 514/822
[58] Field of Search ......................................... 540/200

[56] References Cited

U.S. PATENT DOCUMENTS 4,803,266  2/1989  Kawashima .......................... 540/200

FOREIGN PATENT DOCUMENTS 0264232  9/1987  European Pat. Off. .
62-87562  4/1987  Japan .
62-87563  4/1987  Japan .
63-225353  9/1988  Japan .
63-225354  9/1988  Japan .

*Primary Examiner*—Mark L. Berch
*Attorney, Agent, or Firm*—Lorusso & Loud

[57] ABSTRACT

A 2-azetizinone derivative represented by the formula:

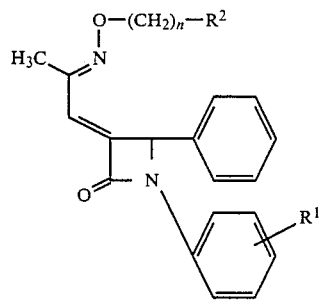

wherein $R^1$ is a halogen atom, an alkyl group having 1 to 4 carbon atoms, an alkoxy group having 1 to 4 carbon atoms or an alkoxycarbonyl group in which the alkoxy group has 1 to 4 carbon atoms, $R^2$ is a group represented by the formula

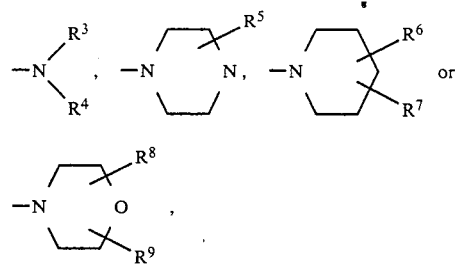

a pyrrolidinyl group or a tetrahydroazepinyl group, and n is an integer of from 2 to 10, and a salt thereof are disclosed. These compounds are useful as blood platelet aggregation inhibiting agent.

3 Claims, No Drawings

3-(SUBSTITUTED PROPYLIDENE)-2-AZETIDINONE DERIVATIVES FOR BLOOD PLATELET AGGRGATION

BACKGROUND OF THE INVENTION

1. Field of the Invention

The present invention relates to 2-azetidinone derivatives having blood platelet aggregation inhibiting activity.

2. Description of the Prior Art

Compounds with an azetidinone skeleton having blood platelet aggregation inhibiting activity are discribed in Japanese Patent Kokai Nos. 62-87562, 62-7563, 63-225353 and 63-225354.

As a result of various researches, the present inventors have found novel 2-azetidinone derivatives having stronger blood platelet aggregation inhibiting activity, and have accompleshed the present invention.

SUMMARY OF THE INVENTION

An object of the present invention is to provide a 2-azetizinone derivative represented by the formula:

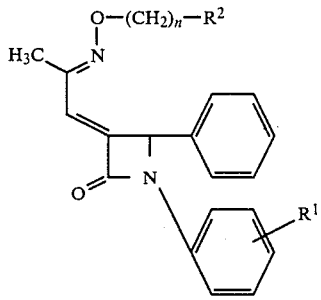

(I)

wherein $R^1$ is a halogen atom, an alkyl group having 1 to 4 carbon atoms, an alkoxy group having 1 to 4 carbon atoms or an alkoxycarbonyl group in which the alkoxy group has 1 to 4 carbon atom, $R^2$ is a group represented by the formula

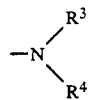

(wherein $R^3$ and $R^4$ are the same or different and are each a hydrogen atom, an alkyl group having 1 to 4 carbon atoms, an alkenyl group having 3 to 5 carbon atoms, a phenyl group or a benzyl group), a group represented by the formula

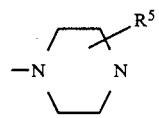

(wherein $R^5$ is a hydrogen atom, a phenyl group substituted by a halogen atom or an alkoxy group having 1 to 4 carbon atoms, a phenyl group, an alkyl group having 1 to 4 carbon atoms or a pyridyl group), a group represented by the formula

(wherein $R^6$ is a hydrogen atom, an alkyl group having 1 to 4 carbon atoms or a benzyl group, and $R^7$ is a hydrogen atom or an alkyl group having 1 to 4 carbon atoms), a group represented by the formula

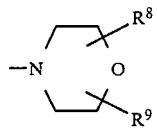

(wherein $R^8$ and $R^9$ are the same or different and each a hydrogen atom or an alkyl group having 1 to 4 carbon atoms), a pyrrolidinyl group or a tetrahydroazepinyl group, and n is an integer of from 2 to 10), and a salt thereof.

DETAILED DESCRIPTION OF THE INVENTION

In the present invention, the alkyl group having 1 to 4 carbon atoms refers to a straight or branched chain alkyl group such as a methyl group, an ethyl group, a propyl group, an isopropyl group and a butyl group. The alkoxy group having 1 to 4 carbon atoms refers to a straight or branched chain alkoxy group such as a methoxy group, an ethoxy group, a propoxy group, an isopropoxy group and a butoxy group. The alkenyl group having 3 to 5 carbon atoms may be an allyl group, a butenyl group, a prenyl group and the like. The halogen atoms may be a fluorine atom, a chlorine atom, a bromine atom or an iodine atom.

The salt means the pharmaceutically acceptable salt such as inorganic or organic acid salts (e.g., hydrochloride, sulfate, acetate, oxalate, maleate and the like).

Configuration of the iminoalkylidene substituent of the compound of the present invention is E-form, and configuration due to the asymmetric carbon atom at the 4-position is dl-form.

Among the preferred compounds of the present invention are (E)-1-(4-methoxyphenyl)-3-{2-[3-(4-morpholinyl)propoxyimino]-propylidene}-4-phenyl-2-azetidinone and (E)-1-(4-methoxyphenyl)-3-[2-[3-{1-[4-(2-pyridyl)piperadinyl]}propoxyimino]propylidene]-4phenyl-2-azetidinone.

The compounds of the present invention can be prepared, for example, by the following method; a 2-azetidinone derivative represented by the formula

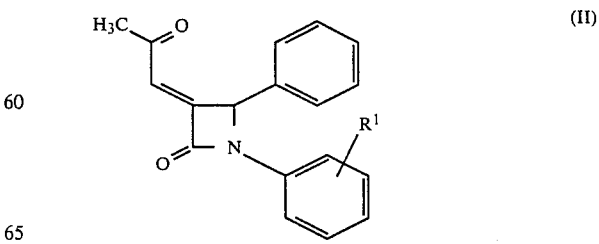

(II)

wherein $R^1$ is as defined above) is reacted with a hydroxylamine derivative represented by the formula $$H_2N-O-(CH_2)_n-R^2 \quad (III)$$

(wherein $R^2$ and n are as defined above) in an inert solvent in the presence of a catalyst to give a compound of Formula I.

Examples of the inert solvent used herein are alcohols (e.g., methanol and ethanol), tetrahydrofuran, chloroform, methylene chloride, benzene, toluene, ethyl acetate, dioxane, xylene and the like. Examples of the catalyst are inorganic acids (e.g., hydrochloric acid gas and sulfuric acid) and the salts thereof, organic acids (e.g., p-toluenesulfonic acid, camphorsulfonic acid and acetic acid) and the salts thereof, amines (e.g., triethylamine and pyridine) and the salts thereof, and magnesium sulfate. The reaction temperature is from 0° C. to the reflux temperature of the solvent, and preferably from room temperature to the reflux temperature of the solvent.

The compound of Formula II can be prepared, for example, by a process described in Japanese Patent Kokai 63-225354.

The compound of Formula III can be prepared, for example, by the following method; a compound represented by the formula $$Cl-(CH_2)_n-R^2 \quad (IV)$$

(wherein $R^2$ and n are as defined above) is first reacted with N-hydroxylphthalimide in an inert solvent in the presence of a base to give a compound represented by the formula

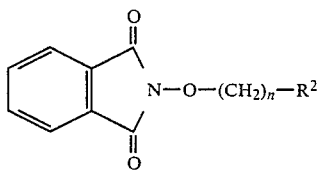

(V)

(wherein $R^2$ and n are as defined above).

Examples of the inert solvent are acetone, N,N-dimethylformamide and dimethyl sulfoxide, and examples of the base are sodium hydride, sodium amide, sodium hydroxide, potassium hydroxide, sodium carbonate, triethylamine and diazabicyclo[5,4,0]unde-7-cene. The reaction temperature is from 0° C. to the reflux temperature of the solvent, and preferably from room temperature to the reflux temperature of the solvent.

The compound of Formula III are also obtained according to an ordinary manner, for example, by treating the compound of Formula V with hydrazine in an inert solvent as described above.

Alternatively, the compound of the present invention can be prepared as follows: 2-azetidinone represented by the formula

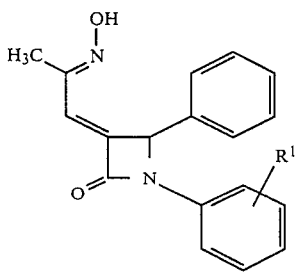

(VI)

(wherein $R^1$ is as defined above) is reacted with a compound of Formula IV in an inert solvent in the presence of a catalyst to give a compound of Formula I.

Examples of the inert solvent used herein are N,N-dimethylformamide, dimethyl sulfoxide, tetrahydrofuran. Examples of the catalyst are amines (e.g., triethylamine and diisopropylethylamine), salts (e.g., sodium carbonate and potassium carbonate) and sodium hydride. The reaction temperature is from 0° C. to the reflux temperature of the solvent, and preferably from 0° C. to the room temperature.

The compound of Formula VI can be prepared by reacting the compound of Formula II with hydroxylamine hydrochloride in an inert solvent in the presence of a catalyst.

Examples of the inert solvent used herein are alcohols (e.g., methanol, ethanol and isopropyl alcohol), tetrahydrofuran, chloroform, benzene and ethyl acetate. Examples of the catalyst are amines (e.g., imidazole and triethylamine), salts (e.g., potassium carbonate, sodium carbonate, sodium acetate and magnesium sulfate). The reaction temperature is from 0° C. to the reflux temperature of the solvent, and preferably from 0° C. to the room temperature.

The compound of the present invention have an excellent blood platelet aggregation inhibiting activity with very poor bleeding tendency as a side-effect, and therefore, they are useful as blood platelet aggregation inhibiting agent. For the purpose, these compounds can be administered orally or parenterally in a conventional dosage form such as tablets, powders, granules, capsules, solutions, suspensions, injectional sulutions and the like, each of which can be prepared by conventional pharmaceutical practices.

The dosage used as a blood platelet aggregation inhibiting agent to human depends on the age, weight, response of patient, administartion route or time of administration, but usually it may be from 0.1 to 3000 mg per day.

The $LD_{50}$ of the compound of Formula I in mouse is more than 5000 mg/kg.

Experiment [Inhibitory effect on acute thrombocytopenia in mice]

Ten male ICR mice weighing 20-30 g were used for each group. Under pentobarbital anaesthesia, adenosine diphosphate (ADP) dissolved in physiological saline in a dose of 1 mg/kg was injected into the tail vein and 20 $\mu$l of blood was collected from the femoral artery at 30 seconds after injection of ADP. Immediately after blood sampling, platelet counts were measured with an automatic blood cell counter (Sysmex CC-180A). Platelet count of normal group without injection of ADP was measured as well.

Test drugs [Compounds 2 and 3 (the compounds of the present invention) and Compound 1 (the comparative drug) in Table 1] were suspended in 5% gum arabic solution and administered by gavage in a dose of 300 mg/kg 2 hours prior to injection of ADP. As control group, 5% gum arabic solution without test drugs was administered.

Inhibition ratio of acute thrombocytopenia was calculated by the following formula.

$$\text{Inhibition ratio (\%)} = \frac{A - B}{C - B} \times 100$$

Note: A: Platelet count of the group treated with both test drug and ADP

B: Platelet count of control group with both 5% gum arabic solution and ADP

C: Platelet count of normal group without injection of ADP

Results are shown in Table 1.

TABLE 1

| Test drug | Inhibition Ratio (%) |
|---|---|
| Compound 1 | 12.00 |
| Compound 2 | 54.66 |
| Compound 3 | 57.61 |

Note; Compound 1: (E)-1-(4-Methoxyphenyl)-3-(2-carboxymethoxyiminopropylidene)-4-phenyl-2-azetidinone Compound 2: (E)-1-(4-Methoxyphenyl)-3-{2-[3-(4-morpholinyl)propoxyimino]propylidene}-4-phenyl-2azetidinone Compound 3: (E)-1-(4-Methoxyphenyl)-3- [2-[3-{1-[4-(2-pyridyl)piperadinyl]}propoxyimino]-propylidene]-4-phenyl-2-azetidinone The present invention is illustrated by the following Reference Example and Examples in more detail.

REFERENCE EXAMPLE 1

To a suspension of 1.75 g of sodium hydride in ml of N,N-dimethylformamide was added a mixture of 11.9 g of N-hydroxyphthalimide and 60 ml of N,N-dimethylformamide, and then the mixture was stirred for minutes. To the reaction solution was added a mixture of 15 g of 3-chloropropyldibutylamine and 10 ml of N,N-dimethylformamide, and then the mixture was heated at reflux for 5 hours. After evaporation of the solvent, ethyl acetate was added to the residue, and the mixture was washed with water. Evaporation of the solvent gave 23.4 g of N-(3-dibutylaminopropoxy)-phthalimide, which was then dissolved in 200 ml of methylene chloride. To the solution was added 20 ml of hydrazine monohydrate, and the mixture was stirred at room temperature for 3 hours. After removal of the insolubles by filtration, the filtrate was concentrated under reduced pressure and distilled under reduced pressure to give 10.3 g of O-(3-dibutylaminopropyl)hydroxylamine.

b.p. 84°–85° C. (0.5 mmHg)

Following a procedure similar to that of Reference Example 1, there were obtained the following compounds.

O-[3-(4-Morpholinyl)propyl]-hydroxylamine.
b.p. 80°–82° C. (0.4 mmHg)

O-[3-(Butylethylamino)propyl]-hydroxylamine.
b.p. 68°–70° C. (0.1 mmHg)

O-[3-(4-Piperidyl)propyl]-hydroxylamine.
b.p. 70° C. (0.6 mmHg)

EXAMPLE 1

Preparation of (E)-1-phenyl-3-{2-[3-(1-piperidyl)-propoxyimino]propylidene}-4-phenyl-2-azetidinone A mixture of 1.11 g of (E)-1-phenyl-3-(2-oxo-propylidene)-4-phenyl-2-azetidinone, 0.63 g of O-[3-(1piperidyl)propyl]-hydroxylamine, 46.5 mg of 10-camphorsulfonic acid and 40 ml of benzene was heated at reflux for 8 hours, and the solvent was evaporated under reduced pressure. The residue was chromatographed on alumina [eluent; hexane-acetone (7:3)] to give the fractions containing the end compound, and the solvent was evaporated. The residue was recrystallized from hexane to give 0.6 g of the title compound. m.p. 120°–122° C.

Following a procedure similar to that of Example 1, there were obtained the following compounds.

(E)-1-(4-Fluorophenyl)-3-{2-[3-(1-piperidyl)-propoxyimino]propylidene}-4-phenyl-2-azetidinone
m.p. 118°–120° C.

(E)-1-(2-Methylphenyl)-3-{2-]3-(1-piperidyl)-propoxyimino]propylidene}-4-phenyl-2-azetidinone oxalate
$^1$H - NMR (CDCl$_3$)δ(ppm); 1.44–1.75 (2H, m), 1.68 (3H, s), 1.80–2.22 (6H, m), 2.36 (3H, s), 2.70–3.40 (6H, m), 4.08 (2H, t), 5.75 (1H, d), 6.71 (1H, d), 6.98–7.20 (4H, m), 7.20–7.45 (5H, m), 8.00 (2H, brs)

(E)-1-Phenyl-3-[2-(3-dibutylaminopropoxyimino)-propylidene]-4-phenyl-2-azetidinone
m.p. 59°–61° C.

(E)-1-(4-Fluorophenyl)-3-[2-(3-dibutylamino)-propylidene]-4-phenyl-2-azetidinone
15 m.p. 62°–64° C.

(E)-1-(2-Methylphenyl)-3-[2-(3-dibutylaminopropoxyimino)propylidene]-4-phenyl-2-azetidinone oxalate
m.p. 69°–71° C.

(E)-1-Phenyl-3-{2-[3-(4-morpholinyl)propoxyimino]propylidene.-4-phenyl-2-azetidinone
m.p. 87°–89° C.

(E)-1-(4-Fluorophenyl)-3-{2-[3-(4-morpholinyl)-propoxyimino]propylidene}-4-phenyl-2-azetidinone
m.p. 121°–123° C.

(E)-1-(4-Fluorophenyl)-3-{2-[3-(4-morpholinyl)-propoxyimino]propylidene}-4-phenyl-2-azetidinone
m.p. 102°–104° C.

(E)-1-(2-Methylphenyl)-3-{2-[3-(4-morpholinyl)-propoxyimino]propylidene}-4-phenyl-2-azetidinone
m.p. 102°–104° C.

(E)-1-Phenyl-3-[2-(3-butylethylaminopropoxyimino)-propylidene]4-phenyl-2-azetidinone
m.p. 76°–79° C.

(E)-1-(4-Fluorophenyl)-3-[2-(3-butylethylamino-propoxyimino)propylidene]-4-phenyl-2-azetidinone
m.p. 76°–79° C.

(E)-1-(2-Methylphenyl)-3-[2-(3-butylethylamino-propoxyimino)propylidene]-4-phenyl-2-azetidinone oxalate
$^1$H - NMR (CDCl$_3$)δ(ppm); 15 0.93 (3H, t), 1.13–1.50 (5H, m), 1.50–1.80 (2H, m), 1.68 (3H, s), 1.92–2.20 (2H, m), 2.35 (3H, s), 2.90–3.30 (6H, m), 4.11 (2H, t), 5.77 (1H, d), 6.72 (1H, d), 7.00–7.23 (4H, m), 7.23–7.50 (5H, m), 8.95 (2H, brs)

(E)-1-(4-Methoxyphenyl)-3-{2-[3-(4morpholinyl)-propoxyimino]propylidene}-4-phenyl-2-azetidinone (Compound 2)
m.p. 106°–108° C.

(E)-1-(4-Methoxyphenyl)-3-{2-[3-(1-piperidyl)-propoxyimino]propylidene}-4-phenyl-2-azetidinone
m.p. 121°–123° C.

(E)-1-(4-Methoxyphenyl)-3-[2-(3-dibutylaminopropoxyimino)propylidene]-4-phenyl-2-azetidinone
m.p. 75°-77° C.

(E)-1-(4-Methoxyphenyl)-3-[2-(3-butylethylaminopropoxyimino)propylidene]-4-phenyl-2-azetidinone
m.p. 79°-81° C.

(E)-1-(4-Methoxycarbonylphenyl)-3-{2-[3-(4morpholinyl)propoxyimino]propylidene}-4-phenyl-2azetidinone
m.p. 169°-170.5° C.

(E)-1-(4-Methoxycarbonylphenyl)-3-[2-(3dibutylaminopropoxyimino)propylidene]-4-phenyl-2azetidinone
m.p. 97°-100° C.

(E)-1-(4-Methoxycarbonylphenyl)-3-{2-[3-(1piperidyl)propoxyimino]propylidene}-4-phenyl-2azetidinone
m.p. 167°-170° C.

(E)-1-(4-Methoxycarbonylphenyl)-3-[2-(3-butylethylaminopropoxyimino)propylidene]-4-phenyl-2-azetidinone
m.p. 95°-97° C.

EXAMPLE 2

Preparation of (E)-1-(4-methôxyphenyl)-3-[2-[3-{1-[4-(2-pyridyl)piperadinyl]}propoxyimino]propylidene]-4-phenyl-2-azetidinone (Compound 3)

(1) To a suspension of 9.2 g of (E)-1-(4-methoxyphenyl)-3-(2-oxopropylidene)-4-phenyl-2azetidinone in 200 ml of isopropyl alcohol were added 3.1 g of hydroxylamine hydrochloride and 3.1 g of imidazole, and then the mixture was stirred at room temperature overnight. The resulting precipitate was collected by filtration, and recrystallized from isopropyl alcohol to give 8.8 g of (E)-1-(4-methoxy-phenyl)-3-(2-hydroxyiminopropylidene)-4-phenyl-2azetidinone.

m.p. 204.5°-206° C.

(2) To a suspension of 0.4 g of sodium hydride in 20 ml of N,N-dimethylformamide was added a mixture of 3.2 g of the compound obtained in the item (1) and 30 ml of N,N-dimethylformamide, and then the mixture was stirred for 5 minutes. To the reaction mixture was added a mixture of 2.4 g of 1-(3-chloropropyl)-4-(2-pyridyl)-piperadine and 20 ml of N,N-dimethylformamide, and the mixture was stirred at room temperature overnight. To the reaction solution was added 200 ml of ethyl acetate, and the mixture was washed 3 times with 200 ml of a saturated aqueous sodium chloride solution After evaporation of the solvent, the residue was recrystallized from a mixture of dichloromethane and hexane to give 2.6 g of the title compound.
m.p. 153°-154.5° C.

Following a procedure similar to that of Example 2, there were obtained the following compounds.

(E)-1-(4-Methoxyphenyl)-3-[2-{3-[4-(3,5-dimethylmorpholinyl)]propoxyimino}propylidene]4-phenyl-2-azetidinone
m.p. 108°-110° C.

(E)-1-(4-Methoxyphenyl)-3- [2-{3-[1-(4-benzylpiperidyl)]propoxyimino}propylidene]-4-phenyl-2azetidinone
m.p. 94.5°-96.5° C.

(E)-1-(4-Methoxyphenyl)-3-[2-(3-benzylethylaminopropoxyimino)propylidene]-4-phenyl-2-azetidinone
m.p. 81°-83° C.

(E)-1-(4-Methoxyphenyl)-3-[2-(3-diisobutylaminopropoxyimino)propylidene]-4-phenyl-2-azetidinone
m.p. 100°-102° C.

(E)-1-(4-Methoxyphenyl)-3-[2-(3-diallylaminopropoxyimino)propylidene]-4-phenyl-2-azetidinone
m.p. 87°-89° C.

(E)-1-(4-Methoxyphenyl)-3- [2-(3-[1-(3,5-dimethylpiperidyl)]propoxyimino}propylidene]-4-phenyl-2-azetidinone
m.p. 114.5°-116.5° C.

(E)-1-(4-Methoxyphenyl)-3-{2-[3-(1pyrrolidinyl)propoxyimino]propylidene}-4-phenyl-2-azetidinone
m.p. 110°-112° C.

(E)-1-(4-Methoxyphenyl)-3-{2-[3-(1-tetrahydroazepinyl)propoxyimino]propylidene}-4-phenyl-2-azetidinone
m.p. 110°-112° C.

(E)-1-(4-Methoxyphenyl)-3-[2-(3-diethylaminopropoxyimino)propylidene]-4-phenyl-2-azetidinone
m.p. 90°-92° C.

(E)-1-(4-Methoxyphenyl)-3-[2-(3-benzylmethylaminopropoxyimino)propylidene]-4-phenyl-2-azetidinone
m.p. 60°-63° C.

(E)-1-(4-Methoxyphenyl)-3- [2-{3-[1-(4-methylpiperadinyl)]propoxyimino}propylidene -4-phenyl-2-azetidinone
m.p. 96°-98° C.

(E)-1-(4-Methoxyphenyl)-3-[2-(3-phenylmethylaminopropoxyimino)propylidene]-4-phenyl-2-azetidinone
m.p. 122°-124° C.

(E)-1)-(4-methoxyphenyl)-3-{2-[2-(4-morpholinyl)ethoxyimino)propylidene]-4-phenyl2-azetidinone
m.p. 96°-98° C.

(E)-1-(4-Methoxyphenyl)-3-{2-[2-(1pyrrolidinyl)ethoxyimino]propylidene}-4-phenyl-2-azetidinone
m.p. 103°-105° C.

(E)-1-(4-Methoxyphenyl)-3- 2- 3-{-[-4-(2methoxyphenyl)piperadinyl]}propoxyimino]propylidene]-4-phenyl-2-azetidinone
m.p. 126'-128° C.

(E)-1-(4-Methoxyphenyl)-3- 2- [3-{1-[4-(4fluorophenyl)piperadinyl]}propoxyimino]propylidene -4-phenyl-2-azetidinone
m.p. 107°-109° C.

(E)-1-(4-Methoxyphenyl[-3-[2-(2-benzylmethylaminoethoxyimino)propylidene]-4-phenyl-2-azetidinone
m.p. 93°-95° C.

(E)-1-(4-Methoxyphenyl)-3-{2-[6-(4morpholinyl)hexyloxyimino]propylidene}-4-phenyl-2-azetidinone
m.p. 86°-88° C.

(E)-1-(4-Methoxyphenyl-3-{2-[6-(1pyrrolidinyl)hexyloxyimino]propylidene}-4-phenyl-2-azetidinone
m.p. 99°-101° C.

(E)-1-(4-Methoxyphenyl)-3-[2-(6-benzylmethylaminohexyloxyimino)propylidene]-4-phenyl-2-azetidinone
m.p. 73°-75° C.

(E)-1-(4-Methoxyphenyl)-3-[2-(6-butylethylaminohexyloxyimino)propylidene]-4-phenyl-2-azetidinone
m.p. 73°-75° C.

What is claimed is:

1. A 2-azetizinone derivative represented by the formula

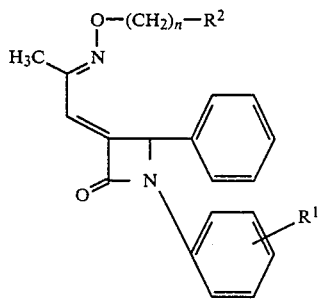

wherein R¹ is a halogen atom, an alkyl group having 1 to 4 carbon atoms, an alkoxy group having 1 to 4 carbon atoms or an alkoxycarbonyl group in which the alkoxy group has 1 to 4 carbon atoms, R² is a group represented by the formula

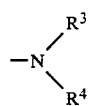

(wherein R³ and R⁴ are the same or different and are each a hydrogen atom, an alkyl group having 1 to 4 carbon atoms, an alkenyl group having 3 to 5 carbon atoms, a phenyl group or a benzyl group), a group represented by the formula

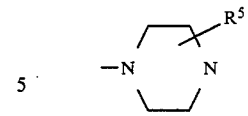

wherein R⁵ is a hydrogen atom, a phenyl group substituted by a halogen atom or an alkoxy group having 1 to 4 carbon atoms, a phenyl group, an alkyl group having 1 to 4 carbon atoms or a pyridyl group), a group represented by the formula

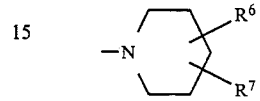

(wherein R⁶ is a hydrogen atom, an alkyl group having 1 to 4 carbon atoms or a benzyl group, and R⁷ is a hydrogen atom or an alkyl group having 1 to 4 carbon atoms), a group represented by the formula

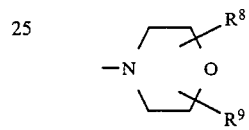

(wherein R⁸ and R⁹ are the same or different and each a hydrogen atom or an alkyl group having 1 to 4 carbon atom), a pyrrolidinyl group or a tetrahydroazepinyl group, and n is an integer of from 2 to 10), and a salt thereof.

2. (E)-1-(4-methoxyphenyl)-3-{2-[3-(4-morpholinyl)-propoxyimino]propylidene}-4-phenyl-2-azetidinone.

3. (E)-1-(4-methoxyphenyl)-3- [2-[3-{1-[4-(2pyridyl)-piperadinyl]}propoxyimino]propylidene]-4-phenyl-2-azetidinone.

* * * * *

UNITED STATES PATENT AND TRADEMARK OFFICE
CERTIFICATE OF CORRECTION

PATENT NO. : 4,952,689

DATED : August 28, 1990

INVENTOR(S) : KAWASHIMA et al

It is certified that error appears in the above-identified patent and that said Letters Patent is hereby corrected as shown below:

Title page:

IN THE TITLE: "AGGRGATION" should read --AGGREGATION--.

Col. 1, line 15, "62-7563" should read --62-87563".

Col. 2, line 52, "4pheynyl" should read --4-phenyl--.

Col. 5, line 32, "2azetidinone" should read --2-azetidinone--;

line 41, before "ml" insert --20--;

line 44, after "for" insert --30--; and line 58, "O-(3-dibutylaminopropyl)hydroxylamine" should read --O-(3-dibutylaminopropyl)-hydroxylamine--.

Col. 6, line 7, "(1piperidyl)" should read --(1-piperidyl)--;

line 21, "(2-]" should read --(2-[--;

line 32, delete "15";

line 37, ".-4-" should read --)-4- --;

delete lines 42-44;

line 57, delete "15";

UNITED STATES PATENT AND TRADEMARK OFFICE
CERTIFICATE OF CORRECTION

PATENT NO. : 4,952,689
DATED : August 28, 1990
INVENTOR(S) : KAWASHIMA et al

It is certified that error appears in the above-identified patent and that said Letters Patent is hereby corrected as shown below:

line 62, "(4morpholinyl)-" should read --(4-morpholinyl)- --.

Col. 7, line 7, "(4mor-" should read --(4-mor- --;

line 9, "2azetidinone" should read --2-azetidinone--;

line 12, "(3dibutylaminopropoxyimino)" should read --(3-dibutylaminopropoxyimino)--;

line 13, "2azetidinone" should read --2-azetidinone--;

line 16, "(1piperidyl)" should read --(1-piperidyl)--;

line 17, "2azetidinone" should read --2-azetidinone--;

line 29, "2azetidinone" should read --2-azetidinone--;

line 35, "(4-methoxy-phenyl)" should read

UNITED STATES PATENT AND TRADEMARK OFFICE
CERTIFICATE OF CORRECTION

PATENT NO. : 4,952,689
DATED : August 28, 1990
INVENTOR(S) : KAWASHIMA et al

It is certified that error appears in the above-identified patent and that said Letters Patent is hereby corrected as shown below:

--(4-methoxyphenyl)--;

line 36, "2azetidinone" should read

--2-azetidinone--;

line 49, after "solution" insert a period --.--;

line 57, "propylidene]4-phenyl-2-" should read

--propylidene]-4-phenyl-2- --; and line 62, "2azetidinone" should read

--2-azetidinone--.

Col. 8, line 10, "(1pyrrolidinyl)-" should read

--(1-pyrrolidinyl)- --;

line 33, "(E)-1)-(4-methoxyphenyl)" should read

--(E)-1-(4-Methoxyphenyl)--;

line 34, "4-phenyl12" should read --4-phenyl-2--;

line 36, "(1pyrrolidinyl)" should read

--(1-pyrrolidinyl)--;

line 39, "3-{-[-4-(2methoxy-" should read

--3-{1-[-4-(2-methoxy- --;

UNITED STATES PATENT AND TRADEMARK OFFICE
CERTIFICATE OF CORRECTION

PATENT NO. : 4,952,689

DATED : August 28, 1990

INVENTOR(S) : KAWASHIMA et al

It is certified that error appears in the above-identified patent and that said Letters Patent is hereby corrected as shown below:

line 43, "4fluoro-" should read --4-fluoro- --;

line 44, after "propylidene" insert --]--;

line 47, "(-4-Methoxyphenyl[" should read --(-4-Methoxyphenyl)--;

line 51, "(-4morpholinyl)" should read --(-4-morpholinyl)--; and line 54, "1pyrrolidinyl)" should read --1-pyrrolidinyl)--.

UNITED STATES PATENT AND TRADEMARK OFFICE
CERTIFICATE OF CORRECTION

PATENT NO. : 4,952,689
DATED : August 28, 1990
INVENTOR(S) : KAWASHIMA et al

It is certified that error appears in the above-identified patent and that said Letters Patent is hereby corrected as shown below:

IN THE CLAIMS:

Col. 10, Claim 3, line 1, "2pyridyl) should read --2-pyridiyl--.

Signed and Sealed this

Eleventh Day of February, 1992

Attest:

HARRY F. MANBECK, JR.

*Attesting Officer*   *Commissioner of Patents and Trademarks*